United States Patent [19]

Hegar

[11] 4,039,523

[45] Aug. 2, 1977

[54] 3-SULFOALKYL-6-HYDROXY-PYRID-(2)-ONE-CONTAINING AZO DYESTUFFS

[75] Inventor: Gert Hegar, Schonenbuch, Switzerland

[73] Assignee: Ciba-Geigy AG, Basel, Switzerland

[21] Appl. No.: 536,130

[22] Filed: Dec. 24, 1974

Related U.S. Application Data

[63] Continuation of Ser. No. 209,350, Dec. 17, 1971, abandoned.

[30] Foreign Application Priority Data

Dec. 22, 1970 Switzerland ............... 19063/70
Feb. 9, 1971 Switzerland ............... 1873/71
Dec. 2, 1971 Switzerland ............... 17614/71

[51] Int. Cl.² ............... C09B 29/36; C09B 62/08; C09B 62/24; C09B 62/50
[52] U.S. Cl. ............... 260/153; 260/146 D; 260/146 T; 260/154; 260/155; 260/156; 260/196; 260/198; 260/206; 260/207; 260/294.81
[58] Field of Search ............... 260/146 T, 146 D, 153, 260/154, 156, 155

[56] References Cited

U.S. PATENT DOCUMENTS

| 3,134,760 | 5/1964 | Schweizer et al. | 260/146 T |
|---|---|---|---|
| 3,169,952 | 2/1965 | Riat et al. | 260/146 T |
| 3,170,911 | 2/1965 | Benz et al. | 260/153 |
| 3,255,173 | 6/1966 | Dehnert et al. | 260/153 |
| 3,340,247 | 9/1967 | Riat et al. | 260/153 |
| 3,344,131 | 9/1967 | Uehlinger | 260/146 T |
| 3,523,115 | 8/1970 | Grandjean | 260/153 |
| 3,640,674 | 2/1972 | Berrie et al. | 260/156 X |
| 3,657,214 | 4/1972 | Berrie et al. | 260/156 |
| 3,663,556 | 5/1972 | Petersen et al. | 260/156 X |
| 3,664,996 | 5/1972 | Berrie et al. | 260/156 |
| 3,725,383 | 4/1973 | Austin et al. | 260/146 T |
| 3,817,975 | 6/1974 | Berrie et al. | 260/156 |
| 3,867,392 | 2/1975 | Heinrich et al. | 260/156 X |

FOREIGN PATENT DOCUMENTS

| 1,200,463 | 7/1970 | United Kingdom | 260/156 |
|---|---|---|---|
| 1,122,389 | 8/1968 | United Kingdom | 260/156 |

*Primary Examiner*—Floyd D. Higel

*Attorney, Agent, or Firm*—Karl F. Jorda; Edward McC. Roberts; Michael W. Glynn

[57] ABSTRACT

An azo dyestuff of the formula

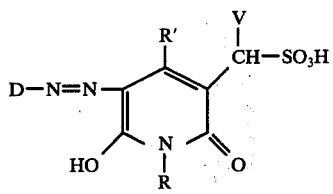

in which D is benzene or naphthalene, optionally substituted by sulfonic acid, carboxy, hydroxy, halogen, nitro, amino, lower alkylamino, lower alkyl, lower alkoxy, lower alkylsulfonyl, trifluoromethyl, cyano, cyclohexyloxycarbonyl, sulfonic acid-N-lower alkylamide, sulfonic acid N-lower alkoxy-loweralkylamide, lower acylamino, phenylazo, sulfophenylazo, sulfonaphthylazo, β-sulfatoethylsulfonyl, β-sulfatoethylsulfonamido, aminosulfonyloxy and a fibre-reactive radical bound via an amino group; or is thiazole, quinoline, benzthiazole, 6-methylbenzthiazole, 1,3,5-thiadiazole or benzisothiazole; R is hydrogen, lower alkyl, lower halogenalkyl, lower hydroxyalkyl, lower acylamino-lower alkyl, phenyl-lower alkyl, phenyl, halogenphenyl, lower alkoxyphenyl, lower acylaminophenyl, lower acylamino-lower alkyl and amino-lower alkyl, in which the amino group is optionally substituted by a fibre-reactive radical; R' is hydrogen, lower alkyl, phenyl-lower alkyl, phenyl, halogenphenyl and lower alkoxy-phenyl; and V is hydrogen, lower alkyl and phenyl, optionally substituted by halogen, nitro, cyano, amino, lower acylamino and a fibre-reactive radical bound via an amino group; and the heavy metal complex compound thereof, is suitable for dyeing and printing widely different types of materials, such as natural and synthetic polyamide and cellulose materials of fibrous structure. These dyestuffs show an excellent building-up capacity and valuable yellow pure and brilliant shades. The dyeings and prints exhibit a good stability to acids and alkalis, a good fastness to light and a good fastness to wet processing.

6 Claims, No Drawings

3-SULFOALKYL-6-HYDROXY-PYRID-(2)-ONE-CONTAINING AZO DYESTUFFS

This is a continuation of our copending application, Ser. No. 209,350, filed Dec. 17, 1971 and now abandoned.

The invention relates to azo compounds which contain the radical of a 3-sulphoalkyl-6-hydroxy-pyrid-(2)-one, especially of the formula

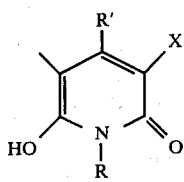

(1)

in which R and R' each represent a hydrogen atom, an alkyl or aryl radical or a heterocyclic radical and X represents a sulphoalkyl group. The radical of the formula (1) is jointed to the radical of a diazo component via an azo bridge. The diazo radical is a heterocyclic or aromatic radical which can itself contain an azo group, or which is derived from a compound of the anthraquinone, nitroaryl, phthalocyanine or stilbene series, or the like. In particular, the diazo radical of the benzene or naphthalene series.

The sulphoalkyl group which is bonded in the 3-position of the pyridone radical is preferably a sulphomethyl group, in particular a group of the formula

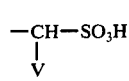

(2)

wherein V represents a low molecular alkyl radical, an optionally substituted aryl or heterocyclic radical or preferably a hydrogen atom.

Where V is an aryl radical it may be substituted by alkyl, or alkoxy groups, halogen atoms, acylamino, amino, cyano, nitro or sulphonic acid groups.

The azo compounds of the invention may exist in several tautomeric forms, but in order to simplify the description the compounds are illustrated in the formula only in one of these tautomeric forms. It must be expressly emphasised, however, that the description both here and hereinafter, especially in the claims, always refers to compounds in any one of these tautomeric forms.

In particular, the term "pyridone" is intended to include both the compounds in question which are substituted at the nitrogen atom of the pyridone ring by a hydrogen atom and the corresponding tautomeric 2,6-dihydroxypyridines.

In addition to the sulphoalkyl group the azo compounds according to the invention can be free from water-solubilizing groups such, for example, as sulphonic acid groups, carboxyl groups, or quaternised amino groups; in particular, however, they can also contain such groups. Above all, the compounds can contain one or more than one reactive radical such, for example, as a halogenotriazine radical, in the molecule. In addition to being substituted by water-solubilising groups, the azo compounds can be substituted, as usual, by still further atoms or groups of atoms, and in particular both in the radical of the diazo component and in the radicals V, R and R', for example by halogen atoms or hydroxyl, amino, alkyl, aryl, alkoxy, aryloxy, acylamino, cyano, acyl, carbalkoxy, acyloxy or nitro groups, and the like. If the radical of the diazo component contains, in the ortho-position to the azo bridge, a complex-forming group such, for example, as a hydroxyl, amino or carboxyl group or an alkoxy group such for example, as a methoxy group, the compounds in question can optionally be converted to their heavy metal complex compounds either before the introduction of reactive radicals or afterwards.

Possible complex-forming metals are, for example, iron, manganese, nickel, copper, cobalt and chromium. The heavy metal complexes can contain one or two molecules of azo compounds containing the radical of the formula (1), joined to a metal atom (1:1- or 1:2-complexes). However, in 1:2-complexes one of the two ligand molecules can also be an azo compound which does not possess the radical of the formula (1) as coupling component, that is to say, for example, a compound of the azo benzene type which contains appropriate complex-forming groups.

Groupings capable of reacting with the hydroxyl groups of cellulose or with the amino groups of polyamides to form a covalent chemical bond, are possible reactive radicals. Such a grouping is, in particular, a low molecular weight alkanoyl or alkylsulphonyl radical substituted by a removable atom or a removable group, a low molecular weight alkenoyl or alkenesulphonyl radical optionally substituted by a removable atom or a removable group, a carbocyclic or heterocyclic radical containing 4-, 5- or 6-rings which is substituted by a removable atom or a removable group and is bonded via a carbonyl or sulphonyl group, or a triazine or pyrimidine radical substituted by a removable atom or a removable group and directly bonded via a carbon atom, or such a grouping contains such a radical. A six-membered heterocyclic radical with two or three ring nitrogen atoms which contains halogen atoms and is bonded via an —NH— group, in particular a chloro-1,3,5-triazine radical, is preferred as the reactive radical.

The invention relates in particular to compounds of the formula

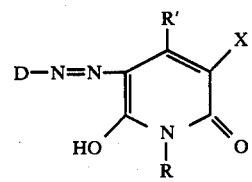

(3)

wherein X represents a sulphomethyl group and R and R' represent hydrogen atoms or alkyl radicals with at most 4 carbon atoms, and wherein D denotes the radical of a diazo component of the benzene or naphthalene series. The invention also relates, in particular, to compounds which possess reactive radicals, above all cyclic reactive radicals, such as, for example, triazine, pyrimidine or cyclobutane radicals, and water-solubilising groups; the reactive radicals can also be contained in the substituents X, R and R'.

A special group of compounds according to the invention are those of the formula (4)

-continued

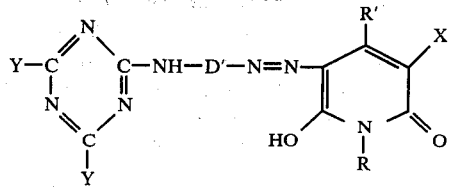

(4)

wherein D' is a sulphobenzene radical, X is a sulphomethyl group one Y is a halogen atom and the other Y is a halogen atom or the radical of the amine, to which a fibre-reactive radical may be bonded, of an alcohol, phenol or mercaptan. The benzene radical can also carry further substituents in addition to one or two sulphonic acid groups as already mentioned.

Particularly valuable compounds are those of the formula (4), wherein D' is a monosulphobenzene radical, in particular such a radical which contains no further substituents other than a sulphonic acid group, X is a sulphomethyl group one Y is a halogen atom and the other Y is the radical of an aminobenzene (or aminonaphthalene)-mono- or disulphonic acid, and R and R' are each a hydrogen atom, a methyl or ethyl radical.

A further group of interesting compounds are those of the formula

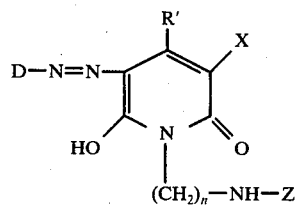

(5)

wherein D is the radical of a diazo component of the benzene or naphthalene series, in particular such a radical which contains water-solubilising substituents, R' is an alkyl or aryl radical, Z is a reactive radical, in particular a dihalogenotriazine radical or a monohalogenotriazine radical which contains the radical of ammonia, an amine alcohol, phenol or mercaptan bonded to a carbon atom, and $n$ is a positive integer, preferably between 1 and 4. Valuable compounds of this type are those of the formula

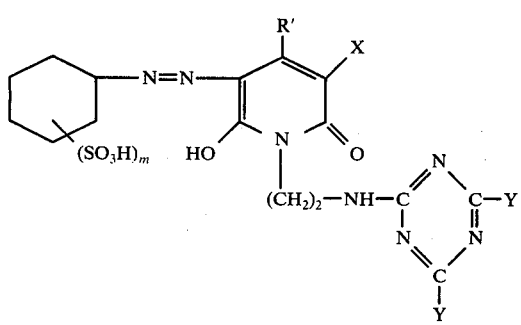

(6)

wherein X is a sulphomethyl group, one Y is a halogen atom, in particular a chlorine or bromine atom and the other Y is the radical of an aminobenzene (or aminonaphthalene)-sulphonic acid, R' is a low molecular weight alkyl radical, in particular a methyl radical, and $m$ is 1 or 2.

A further interesting group of compounds according to the invention are those of the general formula

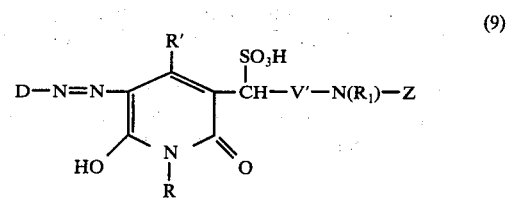

(9)

wherein D represents the radical of a diazo component of the benzene or naphthalene series, especially one that contains water-solubilising substituents, R represents an alkyl, aryl or heterocyclic radical, R' represents an alkyl or aryl radical, V' represents an aromatic radical, especially a phenylene radical, $R_1$ represents a hydrogen atom or a low molecular alkyl radical and Z represents a reactive radical, especially a dihalogenotriazine radical or a monohalogenotriazine radical which contains the radical of ammonia, an amine, alcohol, phenol or mercaptan bonded to a carbon atom. Important compounds of this kind are dyestuffs of the formula

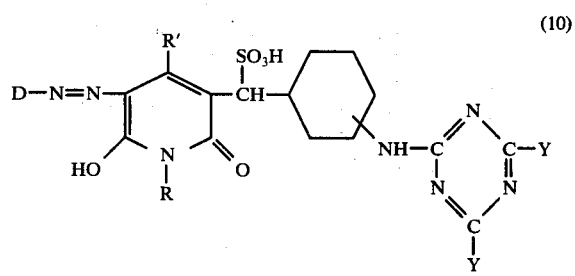

(10)

wherein D represents a sulphophenyl group, R and R' each represent a low molecular alkyl radical, one Y represents a halogen atom, especially a chlorine or bromine atom, and the other Y represents a halogen atom or an amino group, in particular the radical of an aminobenzene (or napthalene)-sulphonic acid.

Importance also attaches to compounds which contain one reactive radical each in the diazo and coupling component, for example compounds of the formulae (9) and (10), which, in addition to the reactive radical Z or the mono- or dihalogenotriazine radical which is bonded to the sulphomethyl group, contain a further reactive radical in the diazo component D.

The manufacture of the azo compounds according to the invention can be carried out by coupling and, where appropriate, metallisation, or by acylation in order to introduce a reactive radical.

The manufacture by coupling is characterised in that a diazo component, in particular a diazo component of the benzene series, is coupled with a 3-sulphoalkyl-6-hydroxypyridone-(2) in particular of the formula

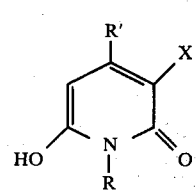

(7)

wherein X, R and R' have the meanings indicated in the explanation of the formula (1), and in that the resulting azo compound is optionally converted into a heavy metal complex by reaction with a heavy metal donor. The starting compounds are preferably diazo components which contain a reactive radical and a water-solubilising group. Possible coupling components of the formula (4) are, in particular, 3-sulphomethyl-1,4-dialkyl-6-hydroxyparid-2-ones.

The diazotisation is carried out by methods which are in themselves known, for example by means of hydrochloric acid and sodium nitrite. The coupling with the pyridone is also carried out according to methods which are in themselves known, in an acid to weakly alkaline medium.

The reaction with the heavy metal donor is carried out according to customary methods, in various solvents, such as, for example, water, ethanol, formamide, glycolethers pyridine and the like, depending on the solubility of the components, optionally at elevated temperature, and in a weakly acid to alkaline medium.

In instead of a compound of the formula (7) which is unsubstituted in the 5-position it is also possible to use as coupling component a compound which contains bonded in the 5-position a group or atoms which is removable under the conditions of the coupling reaction, whereby a coupling in the 5-position is effected. Such coupling components thus correspond to the formula

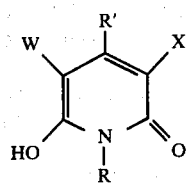
(8)

wherein R and R' each represent a hydrogen atom, an alkyl or aryl radical or a heterocyclic radical, X represents a sulphoalkyl group and W represents a radical which can be removed during the coupling reaction.

As examples of radical which can be removed during the coupling there may be cited carbonamide, carboxylic acid ester, sulphonamide, sulphonic acid ester, sulphonyl and alkylor arylcarbonyl groups. Removable radicals represented by W are in particular carbonamide radicals.

As diazo components which can be employed for the manufacture of the compounds according to the invention having the radical of the formula (1), or the corresponding heavy metal complexes, the diazo compounds of the following amines may be mentioned:
Aminobenzene,
1-Amino-4-chlorobenzene
1-Amino-4-bromobenzene,
1-Amino-4-methylbenzene,
1-Amino-4-nitrobenzene,
1-Amino-4-cyanobenzene,
1-Amino-2,5-dicyanobenzene,
1-Amino-4-methylsulphonylbenzene,
1-Amino-4-carbalkoxybenzene,
1-Amino-2,4-dichlorobenzene,
1-Amino-2,4-dibromobenzene,
1-Amino-2-methyl-4-chlorobenzene,
1-Amino-2-trifluoromethyl-4-chlorobenzene,
1-Amino-2-cyano-4-chlorobenzene,
1-Amino-2-carbomethoxy-4-chlorobenzene,
1-Amino-2-carbomethoxy-4-nitrobenzene,
1-Amino-2-chloro-4-cyanobenzene,
1-Amino-2-chloro-4-nitrobenzene,
1-Amino-2-bromo-4-nitrobenzene,
1-Amino-2-chloro-4-carbethoxybenzene,
1-Amino-2-chloro-4-methylsulphonylbenzene,
1-Amino-2-methylsulphonyl-4-chlorobenzene,
1-Amino-2,4-dinitro-6-methylsulphonylbenzene,
1-Amino-2,4-dinitro-6-(2'-hydroxyethylsulphonyl)-benzene,
1-Amino-2,4-dinitro-6-(2'-chloroethylsulphonyl)-benzene,
1-Amino-2-methylsulphonyl-4-nitrobenzene,
1-Amino-4-methylsulphonyl-2-nitrobenzene,
1-Amino-2,4-dinitrobenzene,
1-Amino-2,4-dicyanobenzene,
1-Amino-2-cyano-4-methylsulphonylbenzene,
1-Amino-2,6-dichloro-4-cyanobenzene,
1-Amino-2,6-dichloro-4-nitrobenzene,
1-Amino-2,4-dicyano-6-chlorobenzene,
4-Aminobenzoic acid cyclohexyl ester,
1-Amino-2,4-dinitro-6-chlorobenzene and in particular 1-Amino-2-cyano-4-nitrobenzene,
1-Aminobenzene-2-, -3- or -4-sulphonamide, such as the N-methyl- or N,N-dimethyl- or -diethylamide,
2-Aminonaphthalene-6-sulphonic acid-N,γ-isopropoxypropylamide,
1-Aminobenzene-2-, -3- or -4-sulphonic acid-N,%(sic)-isopropoxy-propylamide,
1-Aminobenzene-2-, -3- or -4-sulphonic acid-N-isopropylamide,
1-Aminobenzene-2-, -3- or -4-sulphonic acid N,γ-methoxypropylamide,
1-Aminobenzene-2-, -3- or -4-sulphonic acid-N,N-bis(β-hydroxyethyl)-amide,
1-Amino-4-chlorobenzene-2-sulphonomide,
and the N-substituted derivatives,
2-, 3- or 4-aminophenylsulphamate,
2-Amino-4-, -5- or -6-methylphenylsulphamate,
2-Amino-5-methoxy-phenylsulphamate,
3-Amino-6-chlorophenylsulphamate,
3-Amino-2,6-dichlorophenylsulphamate,
4-Amino-2- or -3-methoxyphenylsulphamate,
N,N-Dimethyl-2-aminophenylsulphamate,
N,N-Di-n-butyl-2-aminophenylsulphamate,
N,N-Dimethyl-2-amino-4-chlorophenylsulphamate,
N,N-Propyl-3-aminophenylsulphamate,
N,N-Di-n-butyl-3-aminophenylsulphamate,
O(3-Aminophenyl)-N-morpholino-N-sulphonate,
O(3-Aminophenyl)-N-piperidino-sulphate,
N-Cyclohexyl-O-(3-aminophenyl)-sulphamate,
N(N-Methylanilin)-O-(3-aminophenyl)-sulphonate,
N,N-Diethyl-3-amino-6-methylphenyl-sulphamate,
N-Ethyleneimino-O-(4-aminophenyl)-sulphonate,
N,N-Dimethyl-4-aminophenylsulphamate, O-(n-Propyl)-O-(3-aminophenyl)-sulphonate,
O,β-Chloroethyl-O-(2-aminophenyl)-sulphonate,
O-Benzyl-O- (3-aminophenyl)-sulphonate and,
O-Ethyl-O-(4-amino-2,6-dimethyl-phenyl)-sulphonate,
2-Aminothiazole,
2-Amino-5-nitrothiazole,
2-Amino-5-methylsulphonyl-thiazole,
2-Amino-5-cyanothiazole,
2-Amino-4-methyl-5-nitrothiazole,
3-Amino-5,7-dibromo-benzisothiazole,
3-Amino-5-chloro-benzisothiazole,
5-Amino-4-chloro-benzisothiazole,
3-Amino-5-chloro-7-bromo-benzisothiazole,
3-Amino-5-nitro-benzisothiazole, 2-Amino-4-methylthiazole,
2-Amino-4-phenylthiazole,
2-Amino-4-(4'-chloro)-phenylthiazole,
2-Amino-4-(4'-nitro)-phenylthiazole,
3-Aminopyridine,
3-Aminoquinoline,
3-Aminopyrazole,
3-Amino-1-phenylpyrazole,
3-Aminoindazole,
3-Amino-1,2,4-triazole,
5-(Methyl-, ethyl-, phenyl- or benzyl)-1,2,4-triazole,
3-Amino-1-(4'-methoxyphenyl)-pyrazole,
2-Aminobenzthiazole,
2-Amino-6-methylbenzthiazole,
2-Amino-6-methoxybenzthiazole,
2-Amino-6-chlorobenzthiazole,
2-Amino-6-cyanobenzthiazole,
2-Amino-6-thiocyanobenzthiazole
2-Amino-6-nitrobenzthiazole,
2-Amino-6-carboethoxybenzthiazole,
2-Amino-(4- or -6)-methylsulphonylbenzthiazole,
2-Amino-1,3,4-thiadiazole,
2-Amino-1,3,5-thiadiazole,
2-Amino-4-phenyl- or -4-methyl-1,3,5-thiadiazole,
3-Amino-benzisothiazole,
3-Amino-5-nitro-7-bromo-benzisothiazole,
3,5-Diamino-benzisothiazole,
2-Amino-4-methylthiazole,
2-Amino-4-phenylthiazole,
2-Amino-4-(4'-chloro)-phenylthiazole, 2-Amino-4-(4'-nitro)-phenylthiazole,
3-Aminopyridine,
3-Aminoquinoline,
3-Aminopyrazole
3-Amino-1-phenylpyrazole,
3-Aminoindazole,
3-Amino-1,2,4-triazole,
5-(Methyl-, ethyl-, phenyl- or benzyl)-1,2,4-triazole,
3-Amino-1-(4'-methoxyphenyl)-pyrazole,
2-Aminobenzthiazole,
2-Amino-6-methylbenzthiazole,
2-Amino-6-methoxybenzthiazole,
2-Amino-6-chlorobenzthiazole,
2-Amino-6-cyanobenzthiazole,
2-Amino-6-thiocyanobenzthiazole,
2-Amino-6-nitrobenzthiazole,
2-Amino-6-carboethoxybenzthiazole,
2-Amino- (4- or -6)-methylsulphonylbenzthiazole,
2-Amino-1,3,4-thiadiazole,
2-Amino-1,3,5-thiadiazole,
2-Amino-4-phenyl- or -4-methyl-1,3,5-thiadiazole,
3-Amino-benzisothiazole,
3-Amino-5-nitro-7-bromo-benzisothiazole,
3,5-Diamino-benzisothiazole,
2-Amino-5-phenyl-1,3,4-thiadiazole,
2-Amino-3-nitro-5-methylsulphonyl-thiophene,
2-Amino-3,5-bis-(methylsulphonyl)-thiophene,
5-Amino-3-methyl-isothiazole,
2-Amino-4-cyano-pyrazole and
2-(4'-Nitrophenyl)-3-amino-4-cyanopyrazole,
4-Aminobenzene,
3,2'-Dimethyl-4-aminoazobenzene,
2-Methyl-5-methoxy-4-aminoazobenzene,
4-Amino-2-nitroazobenzene,
2,5-Dimethoxy-4-aminoazobenzene,
4'-Methoxy-4-aminoazobenzene,
2-Methyl-4'-methoxy-4-aminoazobenzene,
3,6,4'-Trimethoxy-4-aminoazobenzene,
4'-Chloro-4-aminoazobenzene,
2'- or 3'-chloro-4-aminoazobenzene,
3-Nitro-4-amino-2',4'-dichloroazobenzene,
4-Aminoazobenzene-4'-sulphonamide,
1- or 2-Aminonaphthalene,
4-Methoxy-5-chloro-2-aminophenol,
6-Acetylamino-4-chloro-2-aminophenol,
6-Nitro-4-chloro-2-aminophenol,
6-Nitro-4-methyl-2-aminophenol,
3-Amino-4-hydroxy-acetophenone,
6-Nitro-4-acetylamino-2-aminophenol
5-Nitro-3-amino-4-hydroxy-acetophenone,
2-Aminophenol-4-carboxylic acid amide,
4,6-Dichloro-2-aminophenol,
3,4,6-Trichloro-2-aminophenol,
4-Nitro-6-chloro-2-aminophenol,
6-Nitro- or 6-chloro-2-aminophenol-4-sulphonamide,
4-Nitro-2-aminophenol-5- or -6-sulphonamide,
2-Aminophenol-5-methylsulphone,
2-Aminophenol,
4- or 5-Nitro-2-aminophenol,
4- or 5-Chloro-2-aminophenol,
4,5-Dichloro-2-aminophenol,
4-Chloro-5-nitro-2-aminophenol,
2-Aminophenol-4- or -5-sulphonic acid,
3,4,6-Trichloroaminophenol,
4-Chloro-2-aminophenol-6-sulphonic acid,
6-Chloro-2-aminophenol-4-sulphonic acid,
4-Nitro-2-aminophenol-6-sulphonic acid,
6-Nitro-2-aminophenol-4-sulphonic acid,
2-Aminophenyl-4,6-disulponic acid,
4,6-Dinitrio-2-aminophenol,
6-Acetylamino-2-aminophenyl-4-sulphonic acid,
4-Acetylamino-2-aminophenol-6-sulphonic acid,
4-Methyl-2-aminophenol,
4-Methoxy-2-aminophenol,
2-Aminophenol-4-sulphonamide,
2-Aminophenol-4-sulphone-N-β-hydroxyethylamide,
2-Aminophenol-4-sulphone-N-methylamide,
2-Aminophenyl-5-sulphonamide,
4-Chloro-2-aminophenol-5- or -6-sulphonamide,
2-Aminophenyl-4-sulphone-N,N-dimethylamide,
2-Aminophenol-4-methylsulphone,
2-Aminophenol-4-ethylsulphone,
6-Acetylamino-4-nitro-2-aminophenol,
2-Aminophenol-4,β-hydroxyethylsulphone,
Anthranilic acid,
2-Amino-3-naphthoic acid,
4- or 5-Chloroanthranilic acid,
4- or 5-Nitroanthranilic acid,
4- or 5-Acetylaminoanthranilic acid,
4- or 5-Sulphoanthranilic acid,
Anthranilic acid-4-sulphonamide,
Anthranilic acid-4- or -5,β-hydroxyethylsulphone,
Anthranilic acid-4- or -5-ethylsulphone,
4-Chloro-2-aminophenol-5-sulphonic acid-N-methylamide,
4- or 5-Benzoylaminoanthranilic acid,
2-Anisidine,
4- or 5-Chloro-2-Anisidine,
4- or 5-Nitro-2-anisidine,
2-Anisidine-4- or -5-sulphonic acid,
2-Methoxy-5-methylaniline,
2,5-Dimethyoxyaniline,
2-Anisidine-4- or -5-β-hydroxyethylsulphone,
2-Amino-1-naphthol-4,8-disulphonic acid,
1-Amino-2-naphthol-4-sulphonic acid,
1-Amino-2-naphthol-4-sulphonamide, 6-Nitro-1-amino-2-naphthol-4-sulphonic acid,
6-Acetylamino-1-amino-2-naphthol-4-sulphonic acid,
4-(2',5'-Disulphophenylazo)-2-methoxy-5-methylaniline,
4-(2',5'-Disulphophenylazo)-2,5-dimethoxyaniline,
4-(2',5'-Disulphophenylazo)-2-methoxy-1-naphthylamino-6-sulphonic acid,
4-(1',5'-Disulphonapth-2'-ylazo)-2,5-dimethoxyaniline,
4-(2',3'- or 4'-Sulphophenylazo)-2-methoxyaniline,
Dianisidine, Benzidine-3,3'-dicarboxylic acid,
4-(2'-, 3'- or 4'-Sulphophenylazo)-2-methoxy-5-methylaniline,
4-(2'-, 3'- or 4'-Sulphophenylazo)-2,5-dimethoxyaniline,
4-(2',5'- or 3',5'-Disulphophenylazo)-2-methoxyaniline,
4-(3',5'-Disulphophenylazo)-2-methoxy-5-methylaniline,
4-(3',5'-Disulphophenylazo)-2,5-dimethoxyaniline,
4-(2'-Carboxy-4'- or -5'-sulphophenylazo)-2-methoxyaniline,
4-(2'-Carboxy-4- or -5'-sulphophenylazo)-2,5-dimethoxyaniline,
4-(2'-Carboxy-4'- or -5'-sulphophenylazo)-2-methoxy-5-methylaniline,
4-(6',8'-Disulphonaphth-2'-ylazo)-2-methoxyaniline,
4-(6',8'-Disulphonaphth-2'-ylazo)-2-methoxyaniline,
4-(6',8'-Disulphonaphth-2'-ylazo)-2-methoxy-5-methoxyaniline,
4-(6',8'-Disulphonaphth-2'-ylazo)-2,5-dimethoxyaniline,
4-Phenylazo-2-aminophenol,
Methanilic acid,
Sulphanilic acid,
Orthanilic acid,
1-Amino-4-methylbenzene-2-sulphonic acid,
Aniline-2,5-disulphonic acid,
2-Naphthylamine-1-sulphonic acid,
2-Naphthylamine-1,5-disulphonic acid,
2-Naphthylamine-4,8-disulphonic acid,
2-Naphthylamine-4,6,8- or 3,6,8-trisulphonic acid,
1-Amino-4-($\beta$-sulphatoethyl-sulphonyl)-benzene,
1-Amino-3-)$\beta$-sulphatoethyl-sulphonyl)-benzene,
1-Amino-2-methoxy-4-($\beta$-sulphatoethylsulphonyl)-5-methylbenzene,
1-Amino-4-($\beta$-sulphatoethylsulphonamido)-benzene,
1-Amino-4-($\beta$-hydroxyethylsulphonyl)-benzene,
1-Amino-4-($\beta$-sulphoethylsulphonylmethylamido)-benzene.

As coupling components there may be cited:
1-Ethyl-3-sulphomethyl-4-methyl-6-hydroxypyridone(2),
1-($\beta$-Hydroxyethyl)-3-sulphomethyl-4-methyl-6-hydroxy-pyridone(2),
1-Methyl-3-sulphomethyl-4-phenyl-6-hydroxypyridone(2),
1-Butyl-3-sulphomethyl-4-methyl-6-hydroxypyridone(2),
1-Ethyl-3-$\alpha$-sulphoethyl-4-hexyl-6-hydroxypyridone(2),
1-Isopropyl-3-$\alpha$-sulphoethyl-4-methyl-6-hydroxypyridone(2),
1,4-Dimethyl-3-sulphomethyl-6-hydroxy-pyridone(2),
1-($\beta$-Methoxyethyl-3-sulphomethyl-4-methyl-6-hydroxy-pyridone(2),
1-Propyl-3-sulphomethyl-4-methyl-6-hydroxypyridone(2),
1-($\beta$-Acetylaminoethyl-3-sulphomethyl-4-methyl-6-hydroxypyridone(2)
1($\gamma$-Dimethylaminopropyl)-3-sulphomethyl-4-methyl-6-hydroxypyridone-(2),
3-Sulphomethyl-4-methyl-2,6-dihydroxypyridine,
3-Sulphomethyl-4-benzyl-2,6-dihydroxypyridine,
1-Ethyl-3-($\alpha$-phenyl)-sulphomethyl-4-benzyl-6-hydroxypyridone(2),
1-Methyl-3-($\alpha$,4'-acetylaminophenyl)-sulphomethyl-4-methyl-6-hydroxypyridone(2),
3-($\alpha$,2'-sulphophenyl)-sulphomethyl-4-phenyl-2,6-dihydroxypyridine.

The coupling components of the formula (7) or (8) which contain a radical of the formula (2), may be obtained by reacting pyridones which are unsubstituted in the 3-position with busulphite adducts of aldehydes, for example in aqueous solution and at normal or elevated temperature.

In order to obtain unitary reaction products, it is also advantageous to use as starting materials pyridones which contain a removable substituent in the 5-position of the pyridone ring, for example a —CN, —COOR or —CONH$_2$ group, and to remove this following the introduction of the sulphoalkyl group by saponification.

A substituent in the 5-position may be advantageously removed also only during the coupling so that — as already mentioned — hydroxyparidones of the formula (8) which are substituted in the 5-position, can be used direct as coupling components. Exemplary of such compounds are:
1,4-Dimethyl-3-sulphomethyl-5-carboethoxy-6-hydroxy-pyridone-(2),
1,4-Dimethyl-3-sulphomethyl-5-acetyl-6-hydroxy-pyridone-(2),
1-Ethyl-4-methyl-3-sulphomethyl-5-acetyl-6-hydroxy-pyridone-(2),
1,4-Dimethyl-3-sulphomethyl-5-benzoyl-6-hydroxy-pyridone-(2),
1,4-Dimethyl-3-$\alpha$-sulphoethyl-5-carbamoyl-6-hydroxy-pyridone-(2),
1-Ethyl-4-isopropyl-3-sulphomethyl-5-carbamoyl-6-hydroxypyridone-(2),
1,4-Diethyl-3-sulphomethyl-5-carbamoyl-6-hydroxy-pyridone-(2),
1-Methyl-4-isopropyl-3-sulphomethyl-5-carbamoyl-6-hydroxypyridone-(2),
1-Ethyl-4-propyl-3-sulphomethyl-5-carbamoyl-6-hydroxy-pyridone-(2),
1-Ethyl-4-methyl-3-sulphomethyl-5-carbamoyl-6-hydroxy-pyridone-(2),
1-Ethyl-4-methyl-3-sulphomethyl-5-N,N-dimethylcarbamoyl-6-hydroxy-pyridone-(2),
1-Ethyl-4-methyl-3-sulphomethyl-5-phenylsulphonyl-6-hydroxy pyridone-(2),
1-Ethyl-4-methyl-3-sulphomethyl-5-sulphamoyl-6-hydroxy-piridone-(2),
4-Methyl-3-sulphomethyl-5-carbamoyl-2,6-dihydroxypyridone,
1,4-Dimethyl-3-sulphomethyl-5-methyl-sulphonyl-6-hydroxy-pyridone-(2),
1,4-Diethyl-3-sulphomethyl-5-methylsulphonyl-6-hydroxy-pyridone-(2),
1-Ethyl-4-methyl-3-sulphomethyl-5-methylsulphonyl-6-hydroxy-pyridone-(2),
1-Ethyl-4-methyl-3-sulphomethyl-5-N-methylcarbamoyl-6-hydroxy-pyridone-(2),
1-Ethyl-3-aminocarbonyl-4-methyl-5-($\alpha$,3'-nitrophenyl)-sulphomethyl-6-hydroxypyridone-(2).

Azo compounds with the radical of formula (1), or the corresponding heavy metal complexes, which contain one or more reactive groups can be manufactured by employing diazo or coupling components which already contain reactive groups. However, in many cases it is possible to introduce reactive groups subsequently into the azo compounds. The introduction can be effected by coupling or by metallisation. Particular interest attaches to these compounds with the radical of the formula (1) which contains a six-membered heterocyclic reactive radical bound via an amino group.

The introduction of the reactive radical is preferably effected by acylating appropriate aminoazo compounds or coupling components which contain an acyltable amino group, or appropriate diazo components, which, in addition to the amino group to be diazotised, still contain a further acylatable amino group, or a group which can be converted to an acylatable amino group, for example by reduction or saponification such, for example, as the nitro group or the acetylamino group.

Appropriate diazo components which, as described above, are suitable for introducing a reactive radical, are, for example:
1,3-Diaminobenzene-4-sulphonic acid,
1,3-Diaminobenzene-4,6-disulphonic acid,
1,4-Diaminobenzene-2-sulphonic acid,
1,4-Diaminobenzene-2,5- or 2,6-disulphonic acid,
1-Amino-4-nitrobenzene,
1-Amino-2-chloro-4-nitrobenzene,
1,3-Diamino-4-methylbenzene-6-sulphonic acid,
6-Acetylamino-4-chloro-2-aminophenol,
6-Nitro-4-methyl-2-aminophenol,
4-Nitro-2-aminophenol-6-sulphonic acid,
6-Acetylamino-1-amino-2-napthol-4-sulphonic acid,
including, for example, compounds already mentioned in the recitation of possible diazo components.

The coupling products, for example, of the above-mentioned diazo components with appropriate pyridones are possible aminoazo compounds which can be introduced into the reactive radicals after the coupling.

The halides or anhydrides of organic acids which contain easily replaceable atoms or groups of atoms are, in particular, possible acylating agents which, in addition to the acylating moiety, also contain a reactive radical.

As an acylating agent containing a reactive radical, the following may for example be mentioned:
Chloro- or bromoacetyl chloride,
β-Chloro- or β-bromopropionyl chloride,
α,β-Dichloro- or α,β-dibromopropionyl chloride,
Chloromaleic acid anhydride,
Carbylsulphate,
Acrylyl chloride,
β-Chloro- or β-bromoacrylyl chloride,
α-Chloro- or α-bromoacrylyl chloride,
α,β-Dichloro- or dibromoacrylyl chloride,
Trichloroacrylyl chloride,
Chlorocrotonyl chloride,
Propiolic acid chloride,
3,5-Dinitro-4-chlorobenzene-sulphonic acid or -carboxylic acid chloride.
3-Nitro-4-chlorobenzene-sulphonic acid or -carboxylic acid chloride,
2,2,3,3-Tetrafluorocyclobutane-1-carboxylic acid chloride,
2,2,3,3-Tetrafluorocyclobutyl-acrylic acid chloride,
β-Chloroethylsulphonyl-endomethylene-cyclohexanecarboxylic acid chloride,
Acrylsulphonyl-endomethylene-cyclohexanecarboxylic acid chloride,
and, above all, heterocyclic acid halides and their derivatives, such as the
2-Chlorobenzoxales carboxylic acid chlorides,
2-Chlorobenzthiazole carboxylic acid chlorides or -sulphonic acid chlorides, and, above all, the following compounds possessing at least 2 nitrogen atoms as heteroatoms of a 6-membered heterocyclic ring:
4,5-Dichloro-1-phenylpyridazonecarboxylic acid chloride or -sulphonic acid chloride,
4,5-Dichloropyridazonepropionic acid chloride,
1,4-Dichlorophthalazinecarboxylic acid chloride or -sulphonic acid chloride,
2,3-Dichloroquinoxalinecarboxylic acid chloride or -sulphonic acid chloride,
2,4-Dichloroquinazolinecarboxylic acid chloride or -sulphonic acid chloride,
2-Methanesulphonyl-4-chloro-6-methylpyrimidine,
Tetrachloropyridazine,
2,4-Bis-methanesulphonyl-6-methylpyrimidine,
2,4,6-Tri- or 2,4,5,6-tetrachloropyrimidine,
2,4,6-Tri- or 2,4,5,6-tetrabromopyrimidine,
2-Methanesulphonyl-4,5-dichloro-6-methylpyrimidine,
2,4-Dichloropyrimidine-5-sulphonic acid, 5-Nitro- or 5-cyano-2,4,6-trichloropyrimidine,
2,6-Bis-methanesulphonylpyridine-4-carboxylic acid chloride,
2,4-Dichloro-5-chloromethyl-6-methyl-pyrimidine,
2,4-Dibromo-5-bromomethyl-6-methyl-pyrimidine,
2,4-Dichloro-5-chloromethylpyrimidine,
2,4-Dibromo-5-bromomethylpyrimidine,
2,5,6-Trichloro-4-methylpyrimidine,
2,6-Dichloro-4-trichloromethylpyrimidine or, in particular
2,4-Bismethylsulphonyl-5-chloro-6-methylpyrimidine,
2,4,6-Trimethylsulphonyl-1,3,5-triazine,
2,4-Dichloropyrimidine,
3,6-Dichloropyridiazine,
3,6-Dichloropyridazine-5-carboxylic acid chloride,
2,6-Dichloro- or 2,6-dibromo-4-carboethoxypyrimidine,
2,4,5-Trichloropyrimidine,
2,4-Dichloropyrimidine-6-carboxylic acid chloride,
2,4-Dichloropyrimidine-5-carboxylic acid chloride,
2,6-Dichloro- or 2,6-dibromopyrimidine-4- or -5-carboxylic acid or -sulphonic acid amides or
-4- or -5-sulphonic acid chloride,
2,4,5,6-Tetrachloropyridazine,
5-Bromo-2,4,6-trichloropyrimidine,
5-Acetyl-2,4,6-trichloropyrimidine,
5-Nitro-6-methyl-2,4-dichloropyrimidine,
2-Chlorobenzthiazole-6-carboxylic acid chloride,
2-Chlorobenzthiazole-6-sulphonic acid chloride,
5-Nitro-6-methyl-2,4-dichloropyrimidine,
2,4,6-Trichloro-5-bromopyrimidine,
2,4,5,6-Tetrafluoropyrimidine,
4,6-Difluoro-5-chloropyrimidine,
2,4,6-Trifluoro-5-chloropyrimidine,
2,4,5-Trifluoropyrimidine,
2,4,6-Trichloro-(-tribromo- or trifluoro)-1,3,5-triazines, and 4,6-dichloro (dibromo- or difluoro)-1,3,5-triazines which are substituted in the 2-position by an aryl or alkyl radical, for example a phenyl, methyl or ethyl radical, or by the radical of an aliphatic or aromatic mercapto compound bonded via the sulphur atom, or by the radical of an aliphatic or aromatic hydroxy compound bonded via the oxygen atom, or, in particular, by an $NH_2$ group or by the radical of an aliphatic, heterocyclic or aromatic amino compound bonded via the nitrogen atom. As such compounds, the radicals of which can be bonded in the 2-position to the triazine nucleus by reaction with trihalogenotriazines, the following may for example be mentioned: aliphatic or aromatic mercapto or hydroxy compounds, such as thioalcohols, thioglycolic acid, thiophenols, alkoxyalkanols, methyl alcohol, ethyl alcohol or isopropyl alcohol, glycolic acid, phenol, chlorophenols or nitrophenols, phenolcarboxylic and phenolsulphonic acids, naphthols, naohtholsulphonic acids and the like, but in particular ammonia and compounds containing amino groups which can be acylated, such as hydroxylamine, hydrazine, phenylhydrazine, phenylhydrazinesulphonic acids, glycolmonoalkyl ethers, methylamine, ethylamine, isopropylamine, methoxyethylamine, methoxypropylamine, dimethylamine, diethylamine, methylphenylamine, ethylenephenylamine, chloroethylamine, ethanolamines, propanolamines, benzylamine, cyclohexylamine, morpholine, piperidine, piperazine, aminocarbonic acid esters, aminoacetic acid ester, aminoethane-sulphonic acid, N-methylaminoethanesulphonic acid, but, above all, aromatic amines, such as aniline, N-methylaniline, toluidines, xylidines, chloroanilines, P- or m-aminoacetanilide, aminophenols, anisidine, phenetidine and, in particular, anilines containing acid groups, sulphanilic acid, methanilic acid, orthanilic acid, anilinedisulphonic acid, aminobenzylsulphonic acid, aniline- -methanesulphonic acid, aminobenzenedicarboxylic acids, naphthylaminomonosulphonic, -disulphonic and -trisulphonic acids, aminobenzoic acids, such as 2-hydroxy-5-aminobenzoic acid, and in addition also colored compounds, or compounds with dyestuff character, for example 4-nitro-4'-aminostilbenedisulphonic acid, 2-nitro-4'-amino-diphenylamino-4,3'-stilbene-disulphonic acid, 2-nitro-4'-aminodiphenylamine-4,3'-disulphonic acid and, in particular, aminoazo dyestuffs or aminoanthraquinones or phthalocyanines which still contain at least one reactive amino group.

The introduction of the substituent in the 2-position of the triazine radical can also be effected after the condensation with the starting diamine or after the reaction, according to the invention, to give the azo compound with the radical of the formula (1).

In addition to the fiber-reactive radicals which can be introduced by acylation, further such radicals which may be mentioned are, for example, the vinylsulphone, the β-sulphato- or thiosulphatoethylsulphone, β-thiosulphatopropionylamide, the β-thiosulphatoethylsulphonylamide or the sulphonic acid-N,β-sulphatoethylamide groups, which are introduced into the diazo component in another way, for example by ester formation or thioester formation.

As compounds which contain a fiber-reactive radical which cannot be introduced by acylation, and in which the fiber-reactive radical is thus preferably not bonded via an amino group, but is bonded directly to the benzene radical, the sulpho esters of the following sulphones may, in particular, be mentioned:
1-Amino-2-methoxy-5-(β-hydroxyethyl)-phenylsulphone,
1-Aminobenzene-3- or -4-β-hydroxyethylsulphone,
1-Amino-2-methyl-benzene-5-β-hydroxyethylsulphone,
1-Amino-4-(β-hydroxyethylsulphonylpropionylaminomethyl)-benzene,
1-Amino-4-(β-hydroxyethylsulphonylamino)-benzene, as well as reactive compounds which can be obtained via the appropriate methylols by Einhorn's method, such as, for example, 1-amino-4-chloroacetylaminomethyl-benzene or 1-amino-3-chloroacetylaminomethyl-benzene-6-sulphonic acid.

The condensation with the acid halides or anhydrides, or with the heterocyclic halogen compounds, is advantageously carried out in the presence of acid-binding agents, such as, for example, sodium carbonate. It is to be understood that all these reactions are to be carried out in such a manner that an unsaturated bond or at least a replaceable halogen atom still remains, in the final product.

The azo compounds obtainable according to the present process and its different variants, as well as their heavy metal complexes, are new; they are suitable for dyeing and printing widely different types of materials, such as, for example, silk, leather, wool, synthetic fibers of polyamides and polyurethanes, polyester fibers or polyacrylonitrile fibers, and polyhydroxylic materials, such as, for example, cellulose-containing materials of fibrous structure, such as linen, cellulose, regenerated cellulose, cotton and the like.

The non-metallised azo compounds according to the invention are particularly important as dyestuffs.

However, the most important compounds are those azo compounds according to the invention which contain a reactive radical and a water-solubilising group, in particular a sulphonic acid group. These dyestuffs are preferably employed for dyeing nitrogen-containing fibers, such as, for example, of super polyamides, super polyurethanes, silk, leather and in particular wool, for example from weakly acid, neutral or weakly alkaline baths, optionally with the addition of customary auxiliaries, for example ethylene oxide condensation products of high molecular weight amines, and, above all, for dyeing cellulose materials, in particular cotton, for example by the exhaustion process from a dilute liquor, from alkaline baths optionally having a high salt content, and in particular by the pad-dyeing process, according to which the article is impregnated with aqueous dyestuff solutions which optionally also contain salt, and the dyestuffs are fixed after an alkali treatment or in the presence of alkali, optionally under the action of heat.

The water-soluble reactive dyestuffs according to the invention show an excellent build-up capacity. They are also suitable for printing, in particular on cotton, and also for printing nitrogen-containing fibers, for example of wool, silk or mixed fabrics containing wool.

The dyeings and prints are distinguished by interesting and valuable yellow, very pure and brilliant shades. The dyeings and prints exhibit a good stability to acids and alkalis, and a good stability to synthetic resin finishing agents, have a good fastness to light and, in particular on cotton, an outstanding fastness to wet processing. The light degree of fixation and the easy removability of non-fixed dyestuff is also worth mentioning.

In order to improve the fastness to wet processing, it is advisable to rinse the dyeings and printings obtained thoroughly with cold and hot water, optionally with the addition of an agent which has a dispersing effect and promotes the diffusion of the non-fixed material.

In the examples which follow, the parts, unless otherwise indicated, denote parts by weight, and the percentages denote percentages by weight. The relationship of parts by weight to parts by volume is the same as of the gram to the $cm^3$.

EXAMPLE 1

A solution of 18.5 parts of cyanuric chloride in 50 parts of acetone is poured into a neutralised solution of 17.3 parts of 1-aminobenzene-3-sulphonic acid in 100 parts of water and 100 parts of ice and during the condensation, the pH is maintained at 6 to 7 by the dropwise addition of 2N sodium hydroxide solution. Upon completion of the condensation a neutral solution of 1,3-diaminobenzene-4-sulphonic acid is added, the solution is heated to 20°-25° C and the pH maintained at 6 to 7 by the dropwise addition of 2N sodium hydroxide solution. As soon as no more diaminobenzenesulphonic acid can be detected in the mixture, 7 parts of sodium nitrite are added and when this has dissolved, the solution is poured on a mixture of 200 parts of ice and 25 parts of concentrated hydrochloric acid. The yellow suspension of the diazo compound is stirred for 1 hour in an ice bath, then a slight excess of nitrous acid is annulled by the addition of aulphamic acid. A solution of 24.7 parts of 1-ethyl-3-sulphomethyl-4-methyl-6-hydroxy-pyridone-2 in 160 parts of water is then poured into this diazo solution. The pH, which is initially 1.5, is raised to 3.5 by the dropwise addition of sodium hydroxide solution, when a clear yellow solution is obtained. This solution is stirred for 1 hour at pH 3.5 in an ice bath and the dyestuff is precipitated by addition of potassium chloride. The resulting dyestuff dyes cotton in pure greenish yellow shades.

The coupling component is prepared as follows:

153 parts of 1-ethyl-4-methyl-6-hydroxy-pyridone-2 are dissolved in 1500 parts of water at pH 8 with the addition of 100 parts of 40% sodium hydroxide solution. To this solution is added dropwise at 30°-35° C within 15 minutes an aqueous solution of the adduct of sodium bisulphate and formaldehyde (prepared by mixing 260 parts of 40% sodium bisulphite solution and 81 parts of 37% formaldehyde solution). The weakly exothermic reaction causes the temperature to rise to about 55° C. The solution is stirred for 1 hour at this temperature, then is acidified with 110 parts by volume of 36% hydrochloric acid and cooled to 5° C. A small amount of crystallized starting material is filtered off after 1 hour, and the residual solution can be used direct for the coupling.

The corresponding compounds containing a sulphomethyl group are obtained if 1,4-dimethyl-6-hydroxy-pyridone or 2,6-dihydroxy-pyridone is used instead of 1-ethyl-4-methyl-6-hydroxy-pyridone Further yellow dyestuffs are obtained when, in accordance with the directions of Example 1, the amines listed in column 1 of the following Table are condensed with cyanuric chloride, the resulting monocondensation products are condensed with the diamines listed in column II, diazotised, and coupled with the coupling components listed in column III.

|    | I<br>Amine | II<br>Diamine | III<br>Coupling Component |
|----|---|---|---|
| 1  | 1-Aminobenzene-3-sulphonic acid | 1,3-Phenylendiamine-4-sulphonic acid | 1-Phenyl-3-sulpho-methyl-4-methyl-6-hydroxypyridone-2 |
| 2  | " | " | 1-Methyl-3-α-sulpho-ethyl-4-methyl-6-hydroxypyridone-2 |
| 3  | 1-Aminobenzene-2-sulphonic acid | " | 1-Ethyl-3-sulphome-thyl-4-methyl-6-hydroxy-pyridone-2 |
| 4  | " | " | 2,6-Dihydroxy-3-sulphomethyl-4-methyl-pyridine |
| 5  | " | " | 1-(2'-Acetylamino-ethyl)-3-sulphomethyl-4-methyl-6-hydroxypyridone-2 |
| 6  | 1-Aminobenzene-4-sulphonic acid | " | 1-Benzyl-3-sulpho-methyl-4-ethyl-6-hydroxypyridone-2 |
| 7  | " | " | 1,4-Dimethyl-3-(α-sulphopropyl)-6-hydroxy-pyridone-2 |
| 8  | 1-Aminobenzene-2,4- | 1,3-Phenylenediamine-4-sulphonic acid | 1-Isopropyl-3-sulpho-methyl-4-methyl-6-hydroxypyridone-2 |
| 9  | 1-Aminobenzene-2,5-disulphonic acid | 1,4-Phenylenediamine-2-sulphonic acid | 2,6-Dihydroxy-4-phenyl-3-sulpho-methylpyridine |
| 10 | 1-Aminobenzene-3,5-disulphonic acid | 1,3-Phenylenediamine | 1-(2'-Hydroxyethyl)-3-sulphomethyl-4-methyl-6-hydroxy-pyridone-2 |
| 11 | 1-Naphthylamine-5-sulphonic acid | 1,3-Phenylenediamine-4,6-disulphonic acid | 1-(4'-Methoxyphenyl)-3-sulphomethyl-4-methyl-6-hydroxy-pyridone-2 |
| 12 | 1-Naphthylamine-6- | " | 1-Ethyl-3-sulpho-methyl-4-propyl-6-hydroxypyridone-2 |
| 13 | 1-Naphthylamine-7-sulphonic acid | " | 1-(2'-Chloroethyl-3-sulphomethyl-4-methyl-6-hydroxypyridone-2 |
| 14 | 1-Naphthylamine-5,7-disulphonic acid | 1,4-Phenylenediamine-2,5-disulphonic acid | 2,6-Dihydroxy-3-sulphomethyl-4-methyl-pyridine |
| 15 | 4-Aminobenzyl-sulphonic acid | 1,3-Phenylenediamine-4-sulphonic acid | 1-Butyl-3-sulphoethyl-4-methyl-6-hydroxy-pyridone-2 |
| 16 | 2-Amino-5-sulpho-benzoic acid | " | 1,4-Diethyl-3-sulpho-methyl-6-hydroxy- |

-continued

| | I<br>Amine | II<br>Diamine | III<br>Coupling Component |
|---|---|---|---|
| 17 | 4-Aminobenzoic acid | 1,3-Phenylenediamine-4,6-disulphonic acid | pyridone-2<br>1-Ethyl-3-sulpho-methyl-4-methyl-6-hydroxypyridone-2 |
| 18 | 2-Aminobenzoic acid | " | 1-Ethyl-3-sulpho-methyl-4-benzyl-6-hydroxypyridone-2 |
| 19 | 1-Aminobenzene-3- and-4-sulphonic acid in the ratio | 1,3-Phenylenediamine-4-sulphonic acid | 1-Methyl-3-sulpho-methyl-4-(4'-chloro-phenyl)-6-hydroxy-pyridone-2 |
| 20 | 1-Aminobenzene-4-β-chloroethyl-sulphone | " | 1-Ethyl-3-sulpho-methyl-4-methyl-6-hydroxypyridone-2 |
| 21 | 1-Amino-3-chloro-acetylaminomethyl-benzene-6-sulphonic acid | " | " |
| 22 | Aniline-N-ω-methane-sulphonic acid | " | " |
| 23 | 3'Amino-2,4-bis-phenylamino-6-chloro-1,3,5-triazi-ne"-sulphonic acid | 1,3-Phenylenediamine-4-sulphonic acid | 1-Ethyl-3-sulpho-methyl-4-methyl-6-hydroxypyridone-2 |
| 24 | 3'-Amino-2,4-bis-phe-nylamino-6-chloro-1,3,5-triazine-4',3"-disulphinic acid | " | " |
| 25 | 1-Aminobenzene-3-sulphonic acid | 1,3-Phenylenediamine-4-sulphonic acid | 1-Ethyl-3-(α-phen-yl)-sulphomethyl-4-methyl-6-hydro-xypyridone-2 |
| 26 | 1-Aminobenzene-2-sulphonic acid | " | 1-Methyl-3-(α,4'-chlorophenyl)-sul-phomethyl-4-methyl-6-hydroxypyridone-2 |
| 27 | Aniline-N-ω-methanesulphonic acid | " | 2,6-Dihydroxy-3-(α,3'-nitrophenyl)-sulphomethyl-4-methyl-6-hydroxy-pyridone-2 |
| 28 | Aniline | " | " |
| 29 | 1-Aminobenzene-3-sulphonic acid | 2,6-Diaminonaphtha-lene-4,8-disulpho-nic acid | " |

EXAMPLE 2

9.4 Parts of 1,3-diaminobenzene-4-sulphonic acid are suspended in 100 parts of water and dissolved by addition of alkali to a pH of 7. To this solution are added at room temperature and with good stirring 10.4 parts of 2-isopropoxy-4,6-dichloro-1,3,5-triazine and the pH is maintained at 6-7 during the condensation by the dropwise addition of 2N sodium hydroxide solution.

Upon completion of the condensation, the condensation mixture is cooled to 0° C, 13 parts by volume of concentrated hydrochloric acid are added, and diazotisation is carried out by the dropwise addition of 50 parts of N sodium nitrite solution. A solution of 11.6 parts of 1,4-dimethyl-3-sulphomethyl-6-hydroxy-pyridone-2 in 60 parts of water is poured into the resulting diazo suspension and the coupling mixture is adjusted to pH 7 by the dropwise addition of 5N sodium hydroxide solution within 1 hour. The dyestuff is isolated from the yellow dyestuff solution by addition of potassium chloride. It dyes cotton in fast yellow shades.

Further yellow dyestuffs having similar properties are obtained if the compound listed in column II of the following Table is used as diamine, that listed in column I as acylating agent, and that listed in column III as coupling component.

| | I | II | III |
|---|---|---|---|
| 1 | 2,4-Dichloro-6-methoxy-1,3,5-triazine | 1,3-Phenylenediamine-4-sulphonic acid | 1-Ethyl-3-sulpho-methyl-4-methyl-6-hydroxypyridone-2 |
| 2 | 2-Amino-4,6-di-chloro-1,3,5-triazine | " | 3-Sulphomethyl-4-methyl-2,6-dihydroxy-pyridine |
| 3 | 2-(2'-Ethoxy)-ethoxy-4,6-di-chloro-1,3,5- | " | 1-Ethyl-3-sulpho-methyl-4-methyl-6-hydroxypyridone-2 |
| 4 | 2,4,5,6-Tetra-chloropyrimidine | " | " |
| 5 | 2,3-Dibromopropi-onic chloride | 1,4-Phenylenediamine-3-sulphonic acid | 1-Methyl-3-sulpho-methyl-4-methyl-6-hydroxypyridone-2 |
| 6 | 2,4-Dichloropyri-midine-5-carboxylic acid chloride | 2,4-Diamino-5-sulpho-benzoic acid | 3-Sulphomethyl-4-methyl-2,6-dihy-droxy pyridine |
| 7 | 2,4-Dichloro-6-phenyl-1,3,5-triazine | 1,3-Diaminobenzene-4,6-disulphonic acid | " |
| 8 | 2,4-Dichloro-6-[5'-(4"-chloro-6"- | 1,3-Phenylenediamine-4-sulphonic acid | " |

-continued

| | I | II | III |
|---|---|---|---|
| | amino)-1,3,5-triazine-2''-yl-amino]-phenyl-amino-1,3,5-triazine-2'-sulphonic acid | | |
| 9 | Chloroacetyl chloride | " | 1-Phenyl-3-sulphomethyl-4-methyl-6-hydroxypyridone-2 |
| 10 | α-Bromacrylic chloride | " | 1,4-Dimethyl-3-sulphomethyl-6-hydroxypyridone-2 |
| 11 | 3,5-Dinitro-4-chlorobenzenesulphonic acid chloride | 1,3-Diaminobenzene-4,6-disulphonic acid | " |
| 12 | 2,2,3,3-Tetrafluorocyclobutane-1-carboxylic acid chloride | " | 3-Sulphomethyl-4-butyl-2,6-dihydroxypyridine |
| 13 | β-Chloroethylsulphonyl-endomethylene-cyclohexanecarboxylic acid chloride | 2,4-Diaminotoluene-5-sulphonic acid | 1-Benzyl-3-α-sulphoethyl-4-methyl-6-hydroxypyridone-2 |
| 14 | 2-Chlorobenzthiazole-carboxylic acid chloride | 1,4-Diamino-5-chlorobenzene-2-sulphonic acid | 1-Ethyl-3-sulphomethyl-4-(4'-methoxyphenyl)-6-hydroxypyridone-2 |
| 15 | 4,5-Dichloropyridazone-propionic chloride | 1,4-Diaminobenzene-2,5-disulphonic acid | 1-Ethyl-3-α-sulphopropyl-4-methyl-6-hydroxypyridone-2 |
| 16 | 2,3-Dichloroquinoxaline-6-sulphonic acid chloride | 1,4-Diaminobenzene-2,6-disulphonic acid | 1-Isopropyl-3-sulphomethyl-4-methyl-6-hydroxypyridone-2 |
| 17 | 2-Methanesulphonyl-4-chloro-6-methyl-pyrimidine | " | 1-Ethyl-3-sulphomethyl-4-methyl-6-hydroxypyridone-2 |
| 18 | 2,4,6-Tribromopyrimidine | 1,3-Diaminobenzene-4-sulphonic acid | 1-Ethyl-3-sulphomethyl-4-methyl-6-hydroxypyridone-2 |
| 19 | 2-Methanesulphonyl-4,5-dichloro-6-methyl-pyrimidine | " | " |
| 20 | 5-Cyano-2,4,6-trichloro-pyrimidine | " | " |
| 21 | 2,6-Bismethanesulphonylpyridine-4-carboxylic acid chloride | " | " |
| 22 | 2,4-Dichloro-5-chloromethyl-6-methylpyrimidine | " | " |
| 23 | 2,4-Bismethylsulphonyl-5-chloro-6-methylpyrimidine | " | " |
| 24 | 2,4,6-Trimethylsulphonyl-1,3,5-triazine | 1,4-Diaminobenzene-2,6-disulphonic acid | 1-Ethyl-3-sulphomethyl-4-methyl-6-hydroxypyridone-2 |
| 25 | 3,6-Dichloropyridazine-5-carboxylic acid chloride | 1,4-Diaminobenzene-2,6-disulphonic acid | 1-(4'-Chlorophenyl)-3-sulphomethyl-4-methyl-6-hydroxypyridone-2 |
| 26 | 2,4-Dichloropyrimidine-6-carboxylic acid chloride | 1,3-Diaminobenzene-4,6-disulphonic acid | 1-(4'-Acetaminophenyl)-3-sulphomethyl-4-methyl-6-hydroxypyridone-2 |
| 27 | 2,4,5,6-Tetrachloropyridazine | " | 1-Ethyl-3-sulphomethyl-4-methyl-6-hydroxypyridone-2 |
| 28 | 2,4,5,6-Tetrafluoropyrimidine | 1,3-Diaminobenzene-4-sulphonic acid | " |
| 29 | 2,4,6-Trifluoro-5-chloropyrimidine | " | " |
| 30 | 2,4,6-Trichloro-1,3,5-triazine | " | " |
| 31 | 2,4-Dichloro-6-methylmercapto-1,3,5-triazine | " | " |
| 32 | 2,4-Dichloro-6-ethyl-1,3,5-triazine | 1,3-Diaminobenzene-4,6-disulphonic acid | 1-Phenyl-3-sulphomethyl-4-methyl-6-hydroxypyridone-2 |
| 33 | 2,4-Dichloro-6-isopropoxy-1,3,5-triazine | " | " |
| 34 | " | 1,3-Diaminobenzene-4-sulphonic acid | 1-Ethyl-3-sulphomethyl-4-methyl-6-hydroxypyridone-2 |
| 35 | " | 1,4-Phenylenediamine-3-sulphonic acid | " |
| 36 | 2-Amino-4,6-dichloro-1,3,5-triazine | 1,3-Diaminobenzene-4-sulphonic acid | 1-Ethyl-3-(α-phenyl)-sulphomethyl-4-methyl-6-hydroxypyridone-2 |
| 37 | 2,4,6-Trichloro-1,3,5-triazine | " | 1-Ethyl-3-(A,4'-acetaminophenyl)-sulphomethyl-4-methyl-6- |

-continued

| | I | II | III |
|---|---|---|---|
| 38 | 2,4-Dichloro-6-isopropoxy-1,3,5-triazine | 1,3-Diaminobenzene-4-sulphonic acid | hydroxypyridone-2 1-Ethyl-3-(α,3'-cyanophenyl)-sulphomethyl-4-methyl)-6-hydroxypyridone-2 |
| 39 | 2,4,6-Trifluoro-5-chloropyrimidine | " | 1,4-Dimethyl-3-(α,3'-nitrophenyl)-sulphomethyl-6-hydroxypyridone-2 |
| 40 | 2,4,6-Tribromo-1,3,5-triazine | " | " |
| 41 | 2-Ethylamino-4,6-dichloro-triazine | " | 1-Ethyl-3-sulphomethyl-4-methyl-6-hydroxypyridone-2 |
| 42 | 2-Morpholino-4,6-dichloro-triazine | " | " |
| 43 | 2-Ureido-4,6-dichlorotriazine | " | " |
| 44 | 2-Dimethylaminosulphonylamino-4,6-dichloro-triazine | " | " |

EXAMPLE 3

To a neutral aqueous solution containing 35.8 parts of the sodium salt of 2-(3'-aminophenyl)amino-4,6-dichloro1,3,5-triazine-4'-sulphonic acid are added 25 parts by volume of a 4N sodium nitrite solution. The whole mixture is cooled to 0° C and 25 parts by volume of concentrate hydrochloric acid are tipped in all at once. Upon completion of the diazotisation, a slight excess of nitrous acid is annulled by addition of sulphamic acid. Into the suspension of the diazo compound is then poured an aqueous solution containing 24 parts of the sodium salt of 2,6-dihydroxy-3-sulphomethyl-4-methylpyridine. The diazo compound passes into solution and a clear yellow dyestuff solution is formed. The pH is adjusted to 7 and then a neutral aqueous solution of 21 parts of the sodium salt of 1,3-phenylenediamine-4-sulphonic acid is added. Condensation is carried out at 20°–25° C, in the course of which the pH of the solution is maintained at 6–7 by the dropwise addition of sodium hydroxide solution. Upon completion of the condensation, the solution is cooled to 0° C and treated with a solution of 18.5 parts of cyanuric chloride in 50 parts of acetone. Condensation is carried out at 0°–5° C, the pH being maintained at 6–7 by the dropwise addition of sodium hydroxide solution. Upon completion of the condensation, 25 parts by volume of a 20% aqueous ammonia solution is added and the batch is stirred for 3 hours at 40° C. The dyestuff of the formula

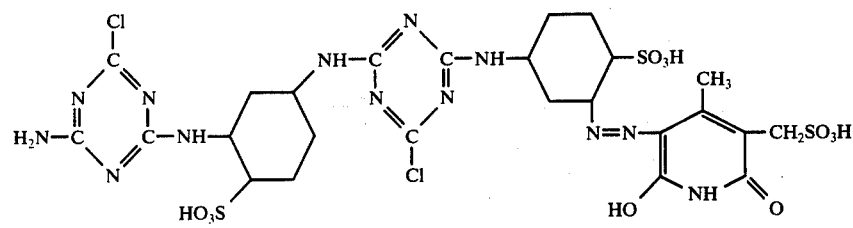

is salted out with sodium chloride, then filtered and dried. It dyes cellulose fibres in fast greenish yellow shades.

EXAMPLE 4

Diazotisation and coupling is carried out as described in Example 3. To the neutral dyestuff solution, which contains the dyestuff of the formula

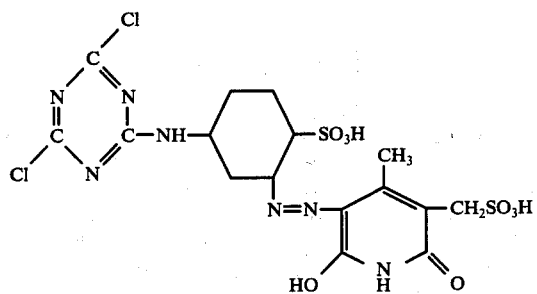

is then added a neutral aqueous solution of 53.3 parts of 1-amino-4-(3'-amino-phenyl)-aminoanthraquinone-2,4'-disulphonic acid. The mixture is heated to 40°–45° C and condensation is carried out at this temperature, the pH being maintained at 6–7 by the dropwise addition of sodium hydroxide solution. Upon completion of the condensation, the dyestuff is isolated by addition of sodium chloride. It dyes cellulose fibre fabrics in pure green shades.

If instead of 1-amino-4-(3'-aminophenyl)-aminoanthraquinone-2,4'-disulphonic acid there is used an equivalent amount of the phthalocyanine dyestuff of the formula

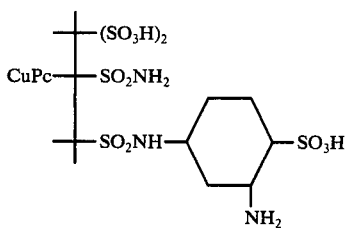

or of the aminoformazane dyestuff of the formula

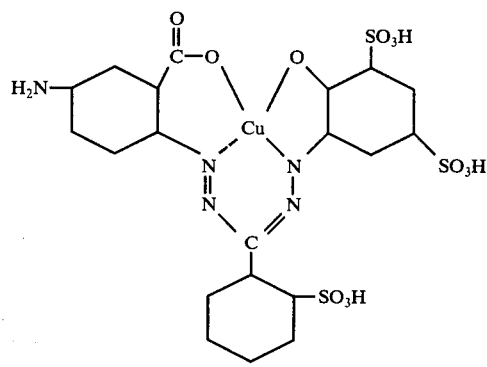

there are obtained likewise dyestuffs which dye cellulose fibre fabrics in fast green shades.

EXAMPLE 5

20 Parts of 1-ethyl-3-aminocarbonyl-4-methyl-6-hydroxy-pyridone-2 in the form of the sodium salt are dissolved in 50 parts of 2N sodium hydroxide solution. The resulting solution is treated with 52 parts of an aqueous solution of the bisulphite adduct of formaldehyde (prepared by mixing 40 parts of 40% sodium bisulphite solution and 12 parts of 37% formaldehyde solution), and the mixture is heated for 1 hour to 80°–90° C, after which time no more starting material is visible in a chromatogram. The resulting solution is cooled and then added to the suspension of the diazo compound, which (according to the directions of Example 1) was obtained from 17.3 parts of 1-aminobenzene-3-sulphonic acid, 18.5 parts of cyanuric chloride and 18.8 parts of 1,3-diaminobenzene-4-sulphonic acid. The pH is adjusted to 8-9 by addition of sodium carbonate and gradually a deep yellow solution is formed. When no more diazo compound can be detected, potassium chloride is added to the solution and the precipitated dyestuff is filtered off. It dyes cotton in pure greenish yellow shades. Investigation in a thin-layer chromatogram shows that the dyestuff so obtained is identical with that of Example 1.

If a diazo compound from the condensation product of 20.8 parts of 2,4-dichloro-6-isopropyl-1,3,5-triazine and 18.8 parts of 1,3-phenylenediamine-4-sulphonic acid and the process is otherwise carried out according to the directions of the Example, there is obtained a dyestuff which likewise dyes cotton in fast greenish yellow shades. Investigation in a thin-layer chromatogram shows that this dyestuff is identical with the dyestuff No. 34 of the table which follows on Example 2.

EXAMPLE 6

17.3 Parts of 2-aminobenzenesulphonic acid are dissolved in 100 parts of water with the addition of 5.5 parts of anhydrous sodium carbonate. The resulting solution is treated with 25 parts by volume of 4N sodium nitrite solution and the entire solution is poured on a mixture of 100 parts of ice and 25 parts by volume of concentrated hydrochloric acid. The suspension of the diazo compounds is adjusted to a pH of 8.5 by addition of 10% sodium carbonate solution. 110 Parts by volume of an aqueous solution containing 31.2 parts of the sodium salt of 1-ethyl-3-sulphomethyl-4-methyl-5-aminocarbonyl-6-hydroxy-pyrid-(2)-one are then added and the pH of the reaction mixture is maintained at 8.5 to 9 during the coupling. Upon completion of the coupling, the dyestuff is precipitated from the yellow dyestuff solution by addition of sodium chloride. It dyes fabrics of synthetic polyamide material in fast greenish yellow shades.

If 27.9 parts of 1-ethyl-3-sulphomethyl-4-methyl-6-hydroxy-pyridone-2 is used as coupling component instead of 1-ethyl- 3-sulphomethyl-4-methyl-5-aminocarbonyl-6-hydroxy-pyridine-2 and the coupling is carried out at a pH of 5 to 6, the identical greenish yellow dyestuff is obtained.

Further dyestuffs which dye fabrics in the shade indicated in column III of the following Table are obtained according to the directions of the Example by dizotising the diazo components listed in column I and coupling them with the coupling components listed in column II.

| | I | II | III |
|---|---|---|---|
| 1 | Aminobenzene | 1-Ethyl-3-sulphomethyl-4-methyl-5-aminocarbonyl-6-hydroxypyridone-2 | yellow on polyamide |
| 2 | 1-Amino-4-chlorobenzene | " | " |
| 3 | 1-Amino-4-nitrobenzene | " | " |
| 4 | 1-Amino-4-methylsulphonylbenzene | 1-Methyl-3-sulphomethyl-4-ethyl-6-hydroxypyridone-2 | " |
| 5 | 1-Amino-2-trifluoromethyl-4-chlorobenzene | " | " |
| 6 | 1-Amino-2-chloro-4-methylsulphonylbenzene | " | " |
| 7 | 1-Amino-2,4-dicyanobenzene | " | " |
| 8 | 4-Aminobenzoic-cyclohexyl ester | " | " |
| 9 | 1-Aminonaphthalene-6-sulphonic acid-N,γ-isopropyloxypropylamide | 1-Isopropyl-3,α-sulphoethyl-4-phenyl-6-hydroxypyridone-2 | " |

-continued

| | I | II | III |
|---|---|---|---|
| 10 | 1-Aminobenzene-4-sulphonic acid -N-isopropylamide | " | " |
| 11 | 4-Aminophenyl-sulphamate | 1-Phenyl-3-sulphomethyl-4-methyl-6-hydroxy-pyridone-2 | " |
| 12 | 2-Aminothiazole | " | " |
| 13 | 2-Aminoquinoline | 1-Ethyl-3-sulphomethyl-4-methyl-6-hydroxypyridone-2 | " |
| 14 | 2-Amino-6-methyl-benzthiazole | " | orange on polyamide |
| 15 | 2-Amino-1,3,5-thiadiazole | " | " |
| 16 | 3-Aminobenziso-thiazole | 1-Ethyl-3-sulphomethyl-4-methyl-6-hydroxypyridone-2 | " |
| 17 | 4-Aminoazobenzene | " | " |
| 18 | 4-Aminoazobenzene 3'-sulphonic acid | " | " |
| 19 | 4-(6',8'-Disulpho-naphth-2'-ylazo)-3-methylaniline | " | " |
| 20 | sulphanilic acid | " | yellow on polyamide |
| 21 | 2-Naphthylamine-1-sulphonic acid | 1-Benzyl-3-sulphomethyl-4-ethyl-5-aminocarbonyl-6-hydroxypyridone-2 | " |
| 22 | 1-Amino-4-(β-sulphatoethyl-sulphonyl)-benzene | 1-Ethyl-3-sulphomethyl-4-phenyl-6-hydroxypyridone-2 | yellow on cotton |
| 23 | 1-Amino-4-(β-sulphatoethyl-sulphonamido)-benzene | 1-Ethyl-3-sulphomethyl-4 methyl-6-hydroxypyridone-2 | " |

EXAMPLE 7

25.3 Parts of aniline-2,5-disulphonic acid are suspended in a mixture of 100 parts of water, 50 parts of ice and 20 parts of concentrated hydrochloric acid and diazotised by the dropwise addition of 25 parts of 4N sodium nitrite solution. To the resulting diazo compound are added 240 parts of an aqueous solution containing 32.6 parts of the sodium salt of 1-(2'-acetaminoethyl)-3-sulphomethyl-4-methyl-6-hydroxy-pyridone2. The pH is adjusted to 4 by the dropwise addition of sodium acetate solution and the yellow dyestuff which has formed is isolated by addition of potassium chloride. It is filtered off and boiled under reflux for 1 hour with 500 parts by volume of N hydrochloric acid in order to remove the acetyl group. After the mixture has cooled, the dyestuff is precipitated by addition of sodium chloride and filtered off. It is dissolved in 500 parts of water and the pH is adjusted to 7 by addition of sodium hydroxide solution. To this neutral dyestuff solution are added, with good stirring, 20 parts of 2,4-dichloro-6-isopropoxy-1,3,5-triazine and condensation is carried out at 25° to 30° C, a pH of 6 to 7 being maintined by the dropwise addition of 2N sodium hydroxide solution. Upon completion of the condensation, the dyestuff is precipitated by addition of potassium chloride. It dyes cellulose fibre fibric in fast, greenish yellow shades.

Greenish yellow dyestuffs which dye cotton with good fastness to wet treatments are likewise obtained if equivalent amounts of 2,3-dibromopropionyl chloride, 2,4,6- trifluoro-5-chloropyrimidine, 2-amino-4,6-dichloro-1,3,5-triazine, 2,4-dichloropyrimidine-5-carboxylic acid chloride or 2-phenylamino-4,6-dichloro-1,3,5-triazine-3'-sulphonic acid are used as acylating agent instead of 2,4-dichloro-6-isopropoxy-1,3,5-triazine.

EXAMPLE 8

64 Parts of the disodium salt of the dyestuff of the formula

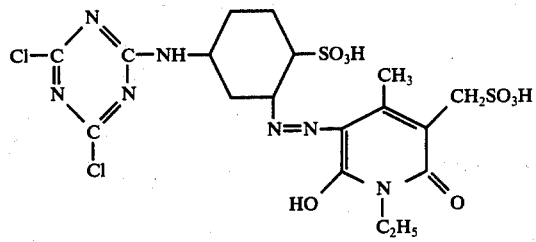

(No. 30 of the Table, Example 2) are dissolved at pH 7 in 1000 parts of water. A solution of 5.4 parts of 1,4-phenylenediamine are added and condensation is carried out at 40° C to 50° C, a pH of 6 to 7 being maintained by addition of 2N sodium hydroxide solution. Upon completion of the condensation, the bis-reactive dyestuff, in which the two reactive groups are linked by a phenylenediamine bridge, is precipitated by addition of sodium chloride. It dyes cotton or regenerated cellulose fibres in pure, strongly greenish yellow shades. Dyestuffs having a similar properties are obtained if instead of 1,4-phenylenediamine there is used as bridging component an equivalent amount of 1,3-phenylenediamine, 1,4- phenylene-diamine-2-sulphonic acid, 4,4'-diamino-stilbene-2,2'-disulphonic acid, 4,4'-diaminodiphenyl-2,2'-disulphonic acid or 4,4'-diaminodiphenylurea-3,3'-disulphonic acid.

EXAMPLE 9

17.3 Parts of 1-aminobenzene- 3-sulphonic acid are dissolved neutral in water by adding sodium hydroxide solution and condensed with 18.5 parts of cyanuric chloride in the conventional manner at 0° to 5° C. Upon completion of the condensation, an aqueous solution of 21 parts of the sodium salt of 1,3-phenylenediamine-4-sulphonic acid is added and condensation is carried out at 25° to 30° C. The condensation solution is subsequently cooled to 0° C, treated with 18.5 parts of cyanuric chloride and condensation carried out at pH 4 to 6 by the dropwise addition of 2N sodium hydroxide solution. A further 21 parts of the sodium salt of 1,3-phenylene diamine-4-sulphonic acid are then added, the temperature is raised to 30° C and condensation is carried out at pH 6 to 7. The resulting solution is cooled to 0° C by the addition of ice, acidified with 25 parts by volume of 30% hydrochloric acid and diazotised by the dropwise addition of 4N sodium nitrite solution until a permanent blue coloration is obtained on potassium iodide starchpaper.

To the yellow diazo solution is added a solution of the sodium salt of 1-ethyl-3-sulphomethyl-4-methyl-6-hydroxypyridone-2 in 100 of water. Upon completion of the coupling, the coupling solution in neutralised to pH 7 by the addition of sodium bicarbonate and the dyestuff is precipitated by sprinkling in potassium chloride. It dyes cotton in fast, greenish yellow shades.

EXAMPLE 10

12.6 Parts of 6-acetylamino-2-aminophenyl-4-sulphonic acid are suspended at 0° C in a mixture of 100 parts of water and 15 parts of 30% hydrochloric acid and diazotised by the dropwise addition of 25 parts of 2N sodium nitrite solution. The resulting diazo suspension is added to a solution of 12.4 parts of 1-ethyl-3-sulphomethyl-4-methyl-6-hydroxypyridone-2 in 50 parts of water, 50 parts of ice and 5.5 parts of sodium hydroxide solution (30%) and the pH is slowly adjusted to 7 by the dropwise addition of sodium hydroxide solution. Upon completion of the coupling, 30 parts of 36% hydrochloric acid are added and the mixture is boiled for 1 hour under reflux to saponify the acetyl group. The crystallised dyestuff, obtained after cooling and salting out with sodium chloride, is filtered off, dissolved in 250 parts of water at pH 7 and treated with a solution of 13 parts of cobalt acetate-tetrahydrate. The batch is boiled for 20 minutes under reflux, then allowed to cool and the cobalt complex is precipitated by addition of sodium chloride. It is dissolved in 500 parts of water at 35° to 40° C and the solution treated with an aqueous solution of 16.1 parts of 2-phenylamino-4,6-dichlorotriazine-3'-sulphonic acid. Condensation is carried out at 35° to 40°, a pH of 6 to 7 being maintained by the dropwise addition of 2N sodium hydroxide solution.

Upon completion of the condensation, the dyestuff is precipitated by addition of potassium chloride. It dyes cellulose fibre material in reddish orange, fast shades.

A dyestuff which dyes cellulose fibres in fast, reddish brown shades is obtained if an equivalent amount of chromium acetate is used instead of cobalt acetate.

EXAMPLE 11

17.3 Parts of 2-aminobenzenesulphonic acid are dissolved in 50 parts of 2N sodium hydroxide solution and 6.9 parts of sodium nitrite are added to the neutral solution. The mixture is poured on a mixture of 100 parts of water, 25 parts of 30% hydrochloric acid and 50 parts of ice. The resulting suspension of the diazo compound is then added to a solution of 44.5 parts of the sodium salt of the condensation product of 1-ethyl-3-aminocarbonyl-4-methyl-6-hydroxypyridone-2 and the bisulphite adduct of 4-amino-benzaldehyde in 250 parts of water. The pH is adjusted to 9 by addition of 20 parts of sodium carbonate and the mixture is stirred at 5° to 10° C until the coupling is completed. The dyestuff is precipitated from the resulting yellow dyestuff solution by the addition of sodium chloride. It is collected by section filtration, dissolved in 500 parts of N hydrochloric acid and the solution is heated for 2 hours to 85°–90° C to saponify the acetyl group. The dyestuff is filtered off after the solution has cooled, washed with a 10% saline solution and dried.

26 Parts of the so obtained dyestuff of the formula

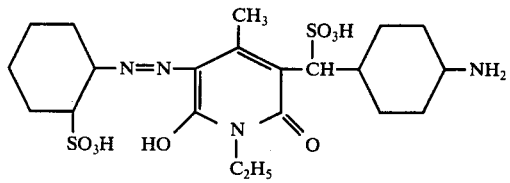

are dissolved in 400 parts of water with the addition of sodium hydroxide at pH 7, in the form of the disodium salt. 10.4 Parts of 2-isopropoxy-4,6-dichloro-1,3,5-triazine are added, the mixture is heated to 30° C and the pH of the solution is maintained at 6.8 to 7 during the condensation by the dropwise addition of N sodium hydroxide solution. Upon completion of the condensation, the dyestuff is precipitated by addition of a mixture of sodium chloride and potassium chloride, filtered off and dried. It dyes cellulose fibre fabric in pure, greenish yellow shades.

Dyestuffs which likewise dye cellulose fibres in fast, greenish yellow shades are obtained if instead of 2-isopropoxy-4,6-dichloro-1,3,5-triazine there are used equivalent amounts of 2-amino-4,6-dichloro-1,3,5-triazine, 2,4,5,6-tetrachloropyrimidine or 2,4,6-trifluoro-5-chloropyrimidine.

EXAMPLE 12

A solution of 18.5 parts of cyanuric chloride in 50 parts of acetone is poured into a neutralised solution of 17.3 parts of 1-aminobenzene-3-sulphonic acid in 100 parts of water and 100 parts of ice and the pH is maintained at 6 to 7 during the condensation by the dropwise addition of 2N sodium hydroxide solution. Upon completion of the condensation a neutral solution of 1,3-diaminobenzene-4-sulphonic acid is added, the mixture is heated to 20°–25° C and the pH of the solution is maintained at 6 to 7 by the dropwise addition of 2N sodium hydroxide solution. As soon as no further diaminobenzenesulphonic acid can be detected in the mixture, 7 parts of sodium nitrite are added and when this has dissolved, the whole mixture is poured on a mixture of 200 parts of ice and 25 parts of concentration hydrochloric acid. The yellow suspension of the diazo compound is stirred for 1 hour in an ice bath; then a slight excess of nitrous acid is annulled by addition of sulphamic acid. A solution of 35 parts of the coupling component of the formula

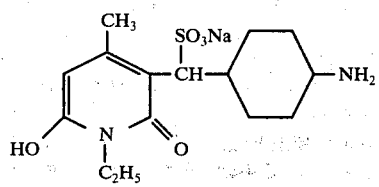

in 250 parts of water (prepared by reacting 1-ethyl-4-methyl-6-hydroxypyridone-2 with the bisulphite adduct of 4-acetaminobenzaldehyde and subsequently saponifying the acetyl group by boiling the reaction product for 2 hours in Nhydrochloric acid) is then poured into this diazo suspension. 2N sodium hydroxide solution is added at 0° to 5° C until the pH has resin to 7. To the neutral yellow dyestuff solution are then added 21 parts of 2,4,5,6-tetrachloropyrimidine and the resulting suspension is heated to 40° to 45° C. The pH is maintained at 6 to 7 during the condensation by the dropwise addition of 2N sodium hydroxide solution. When all the tetrachloropyrimidine has been consumed, the bis-reactive dyestuff is precipitated from the clear yellow dyestuff solution by the addition of sodium chloride. It dyes cotton in fast, greenish yellow shades.

Valuable greenish yellow dyestuffs are likewise obtained if instead of 2,4,5,6-tetrachloropyrimidine there are used equivalent amounts of 2,4,6-trichloropyrimidine, 2,4,6-trifluoro-5-chloropyrimidine, 2-amino-4,6-dichloro-1,3,5-triazine, 2-ureido-4,6-dichloro-1,3,5-triazine, or chloroacetyl chloride.

EXAMPLE 13

44.5 Parts of the aminoazo dyestuff of the formula

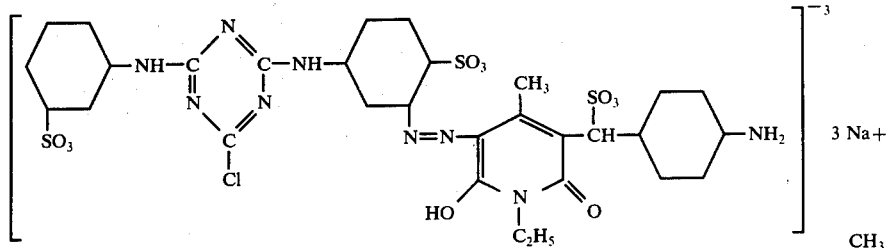

(prepared by diazotisation of 2-(3'-aminophenylamino-4-phenylamino-6-chloro-1,3,5-triazine-4',3''-disulphonic acid and coupling with 1-ethyl-3-(α-sulpho-α,4'-aminophenyl)-methyl-4-methyl-6-hydroxypyridone-2) are dissolved in 300 parts of water at 40° C. Phosgene is passed into this dyestuff solution until no more free amino groups can be detected in the reaction mixture, the pH of the mixture being maintained at 7 to 7.5 by the dropwise addition of 2N sodium hydroxide solution. Upon completion of the reaction, the resulting bis-reactive dyestuff is precipitated with sodium chloride, collected by suction filtration and dried. It dyes cotton in fast, greenish yellow shades.

A dyestuff which likewise dyes cotton in greenish yellow shades in obtained by condensing in like manner 2 mols of the amino dyestuff of the above formula with 1 mol of fumaric dichloro, the condensation being carried out at a pH of 6 to 7.

If instead of phosgene or fumaric dichloride there is used an equivalent amount of cyanuric chloride and condensation is carried out in the ratio of 2 mols of dyestuff to 1 mol of cyanuric chloride, a dyestuff is obtained which contains on analysis 3 reactive chlorine atoms.

EXAMPLE 14

44.5 Parts of the aminoazo dyestuff cited in Example 12 are dissolved in 300 parts of water and the solution is cooled to 0° C. To this solution are added 9.25 parts of cyanuric chloride and the pH is maintained at 7 by the dropwise addition of 2N sodium hydroxide solution. Upon completion of the condensation, a solution of 3.05 parts of 2,5-diaminotoluene in 25 parts of water is poured in. The mixture is is heated to 40°-45° C and this temperature is maintained until the condensation is complete, a pH of 7 being kept by the dropwise addition of 2N sodium hydroxide solution. The resulting dyestuff is Precipitated by addition of sodium chloride, collected by suction filtration and dried. It dyes cotton in greenish yellow shades.

Further dyestuffs with similar tinctorial properties are obtained if instead of 2,5-diamino-toluene there are used equivalent amounts of 1,4- or 1,3-diaminobenzene, 2,4-diaminotoluene, 2,5-diaminobenzoic acid, 4,4'-diamino-diphenylurea-2,2'-disulphonic acid or glycol-bis-4-aminophenylether.

EXAMPLE 15

18.5 Parts of cyanuric chloride are added at 0° C and a pH of 5 to 350 parts by volume of an aqueous solution containing 35 parts of pyridone coupling component of the formula

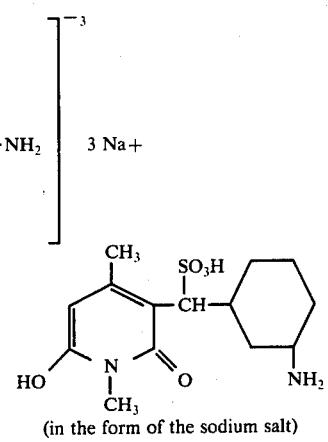

(in the form of the sodium salt)

and the mixture is stirred at this temperature, a pH is 4 to 5 being maintained by the dropwise addition of dilute sodium hydroxide solution. Upon completion of the condensation, a diazo solution of 25.3 parts of aniline-2,4-disulphonic acid which is prepared in the convention manner is added, the pH is adjusted to 6 by the dropwise addition of sodium hydroxide solution and the mixture is stirred until the coupling is complete. To the yellow dyestuff solution are added 25 parts by volume of 24% aqueous ammonia solution and the mixture is then stirred for 3 hours at 30° to 35° C. The dyestuff is precipitated from the solution by the addition of a mixture of sodium chloride and potassium chloride. It dyes cotton in fast, greenish yellow shades.

The coupling component is obtained by heating for 1 hour equivalent amounts of 1,4-dimethyl-6-hydroxypyridone-2 and the bisulphite adduct of 3-aminobenzaldehyde in aqueous solution to 60° C.

The same dyestuff is also obtained when, after the conde condensation with cyanuric chloride, condensation with ammonia is first carried out and then coupling.

DYEING INSTRUCTION I

2 Parts of the dyestuff of Example 1, 1st. paragraph, are dissolved in 100 parts of water.

A cotton fabric is impregnated on a padder with this solution, and the excess liquid is squeezed out so that the material retains 75 % of its weight of dyestuff solution.

The article thus impregnated is dried, then impregnated at room temperature in a solution which contains, per liter, 10 g of sodium hydroxide and 300 g of sodium chloride, squeezed out to 75% liquid uptake, and steamed at 100 to 101° C for 60 seconds. The article is then rinsed, soaped at the boil for quarter of an hour in a 0.3% strength solution of and ion-free detergent, rinsed and dried.

A fixed dyeing which is fast to boiling is obtained. If a cellulose fabric is used instead of a cotton fabric, a similary good result is obtained.

PRINTING INSTRUCTION

2 Parts of the dyestuff obtained according to Example 2 are mixed with 20 parts of urea, dissolved in 28 parts of water, and stirred into 40 parts of a 5% strength sodium alginate thickener. 10 Parts of a 10% strength sodium carbonate solution are then added.

A cotton fabric is printed on a roller printing machine using this printing ink, is dried, and the print obtained is steamed at 105° C for 8 minutes. The printed fabric is then thoroughly rinsed in cold and hot water and dried.

I claim:

1. An azo dyestuff of the formula

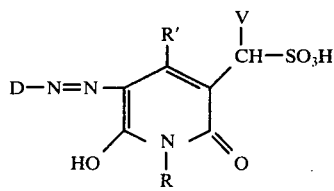

in which

D is benzene or naphthalene, unsubstituted or substituted by sulfonic acid, carboxy, hydroxy, chloro, bromo, $NH_2$—, lower alkylamino, lower alkyl, lower alkoxy, lower alkylsulfonyl, trifluoromethyl, cyano, cyclohexyloxycarbonyl, sulfonic acid-N-lower alkylamide, sulfonic acid-N-lower alkoxyloweralkylamide, acetylamino, phenylazo, sulfophenylazo, sulfonaphthylazo, β-sulfatoethylsulfonyl, aminosulfonyloxy or a fibre-reactive radical capable of reacting with the hydroxyl groups of cellulose or the amino groups of polyamides and bound via an amino group; or is thiazole, quinoline, benzthiazole, 6-methylbenzthiazole, 1,3,5-thiadiazole or benzisothiazole;

R is hydrogen, lower akyl, lower chloroalkyl, lower hydroxyalkyl, acetylamino-lower alkyl, phenyl-lower alkyl, phenyl, chlorophenyl, lower alkoxyphenyl, acetaminophenyl or amino-lower alkyl, in which the amino group is unsubstituted or substituted by a fibre-reactive radical capable of reacting with the hydroxyl groups of cellulose or the amino groups of polyamides;

R' is hydrogen, lower alkyl, phenyl-lower alkyl, phenyl, chlorophenyl or lower alkoxy-phenyl; and V is hydrogen, lower alkyl or phenyl, unsubstituted or substituted by chloro, nitro, cyano, $mNH_2$— or a fibre-reactive radical capable of reacting with the hydroxyl groups of cellulose or the amino groups of polyamides and bound via an amino group; and the heavy metal complex compound thereof selected from the group consisting of iron, manganese, nickel, copper, cobalt and chromium.

2. An azo dyestuff as claimed in claim 1 of the formula

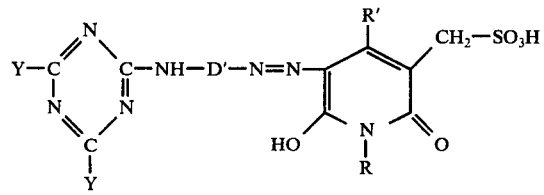

in which D' is sulfobenzene, R and R' each is hydrogen or alkyl with 1 to 4 carbon atoms, one Y is chloro or bromo and the other Y is chloro, bromo, amino, phenylamino, sulfophenylamino, sulfonaphthylamino, carboxyphenylamino, alkoxy with 1 to 4 carbon atoms, alkoxyalkoxy with 1 to 8 carbon atoms, alkylmercapto with 1 to 4 carbon atoms, alkylamino with 1 to 4 carbon atoms, ureido, morpholino, or a residue of the formula

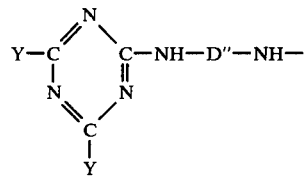

in which D' is phenylene or sulfophenylene or a residue of the formula

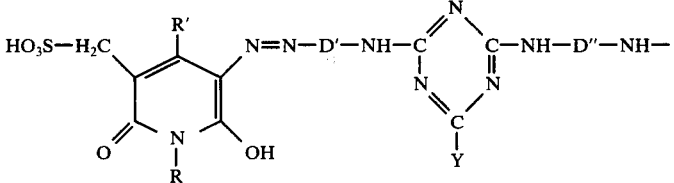

in which D', R and R' are as defined above; D" is phenylene, sulfophenylene, sulfostilbene, sulfodiphenyl or sulfodiphenylurea.

3. An azo dyestuff as claimed in claim 1 of the formula

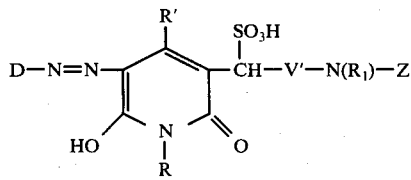

in which

D, R and R' are as defined in claim 1,

V' is phenylene,
$R_1$ is hydrogen or lower alkyl and
Z is a fibre-reactive radical capable of reacting with the hydroxyl groups of cellulose or the amino groups of polyamides.

4. An azo dyestuff as claimed in claim 1 of the formula

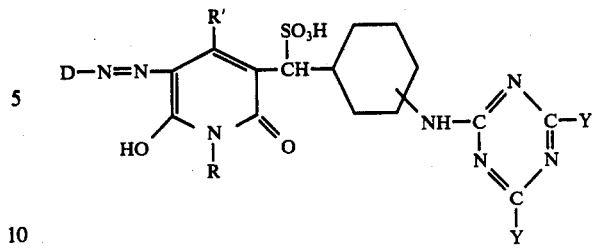

in which
D is sulfobenzene,
R and R' each is lower alkyl and
one Y is chloro or bromo and the other Y is chloro, bromo, amino, phenylamino, sulfophenylamino, sulfonaphthylamino, carboxyphenylamino, alkoxy with 1 to 4 carbon atoms, alkoxyalkoxy with 1 to 8 carbon atoms, alkylmercapto with 1 to 4 carbon atoms, alkylamino with 1 to 4 carbon atoms, ureido and morpholino.

5. The azo dyestuff as claimed in claim 2 of the formula

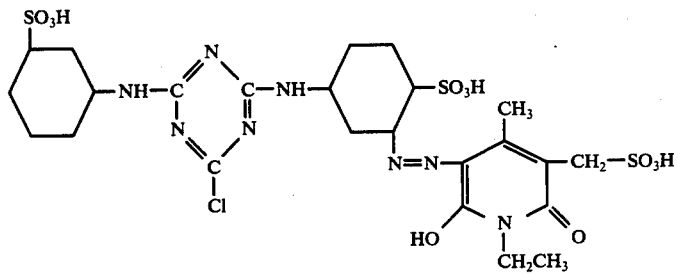

6. The azo dyestuff as claimed in claim 2 of the formula

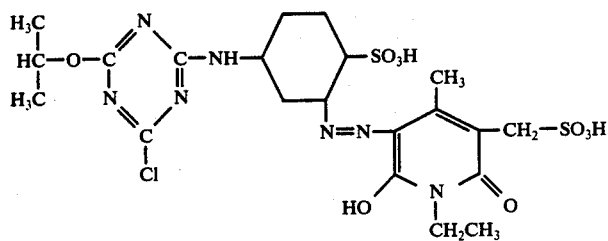

* * * * *

UNITED STATES PATENT OFFICE
CERTIFICATE OF CORRECTION

Patent No. 4,039,523     Dated August 2, 1977

Inventor(s) Gert Hegar

It is certified that error appears in the above-identified patent and that said Letters Patent are hereby corrected as shown below:

Col. 32 - line 6, after "cyano," delete "m".

Signed and Sealed this

First Day of November 1977

[SEAL]

Attest:

RUTH C. MASON
Attesting Officer

LUTRELLE F. PARKER
Acting Commissioner of Patents and Trademarks